(12) United States Patent
Eghbal et al.

(10) Patent No.: US 8,991,034 B2
(45) Date of Patent: Mar. 31, 2015

(54) METHODS OF MANUFACTURING A COMPLIANT DIAPHRAGM MEDICAL SENSOR

(71) Applicant: Covidien LP

(72) Inventors: Darius Eghbal, Oakland, CA (US); William Raridan, Pleasanton, CA (US); Joseph Coakley, Dublin, CA (US); George L. Matlock, Pleasanton, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/657,181

(22) Filed: Oct. 22, 2012

(65) Prior Publication Data

US 2013/0048194 A1    Feb. 28, 2013

Related U.S. Application Data

(60) Division of application No. 12/491,061, filed on Jun. 24, 2009, now Pat. No. 8,311,602, which is a division of application No. 11/495,411, filed on Jul. 28, 2006, now Pat. No. 7,574,244, which is a continuation of application No. 11/199,345, filed on Aug. 8, 2005, now Pat. No. 7,657,294.

(51) Int. Cl.
*H05K 13/00* (2006.01)
*A61B 5/00* (2006.01)
*A61B 5/1455* (2006.01)

(52) U.S. Cl.
CPC ........... *A61B 5/6826* (2013.01); *A61B 5/14552* (2013.01); *A61B 5/6838* (2013.01)
USPC ........................................ 29/592.1; 600/344

(58) Field of Classification Search
CPC ............ A61B 5/14552; A61B 5/4869; A61B 5/6826; A61B 5/6838
USPC ....... 29/592.1–595; 73/272 R, 721, 754, 862, 73/626; 606/151, 344; 600/485, 322–323, 600/344, 549; 156/292
See application file for complete search history.

(56) References Cited

U.S. PATENT DOCUMENTS 5,090,410 A    2/1992    Saper et al.
5,170,786 A    12/1992    Thomas et al.
(Continued)

FOREIGN PATENT DOCUMENTS

CN    11080192    11/2007
DE    10030862 A1    1/2002
(Continued)

OTHER PUBLICATIONS

International Search Report from PCT application No. PCT/US2006/030674 dated Nov. 1, 2007, 3 pps.

*Primary Examiner* — Minh Trinh
(74) *Attorney, Agent, or Firm* — Fletcher Yoder PC

(57) ABSTRACT

A method for manufacturing a sensor is provided. The method includes providing a frame having a loop structure, and covering the frame with a coating material to provide a sensor body having at least one diaphragm structure. The one or more diaphragm structures of the sensor body bias an emitter housing and a detector housing of the frame toward one another. The sensor may be placed on a patient's finger, toe, and so forth, to obtain pulse oximetry or other physiological measurements.

20 Claims, 6 Drawing Sheets

(56) References Cited

U.S. PATENT DOCUMENTS

| | | | |
|---|---|---|---|
| 5,247,932 A | 9/1993 | Chung et al. | |
| 5,413,099 A | 5/1995 | Schmidt et al. | |
| 5,413,102 A | 5/1995 | Schmidt et al. | |
| 5,437,275 A | 8/1995 | Amundsen et al. | |
| 5,452,717 A | 9/1995 | Bramigan et al. | |
| 5,465,714 A * | 11/1995 | Scheuing | 600/323 |
| 5,507,286 A | 4/1996 | Solenberger | |
| 5,619,992 A | 4/1997 | Guthrie et al. | |
| 5,673,693 A | 10/1997 | Solenberger | |
| 5,810,724 A | 9/1998 | Gronvall | |
| 5,895,871 A * | 4/1999 | Patton et al. | 73/866.5 |
| 5,910,108 A | 6/1999 | Solenberger | |
| 6,029,530 A * | 2/2000 | Patton et al. | 73/866.5 |
| 6,144,868 A | 11/2000 | Parker | |
| 6,253,098 B1 | 6/2001 | Walker et al. | |
| 6,321,100 B1 | 11/2001 | Parker | |
| 6,343,224 B1 | 1/2002 | Parker | |
| 6,349,228 B1 | 2/2002 | Kiani | |
| 6,519,487 B1 | 2/2003 | Parker | |
| 6,553,243 B2 | 4/2003 | Gurley | |
| 6,671,531 B2 | 12/2003 | Al-Ali et al. | |
| 6,681,126 B2 | 1/2004 | Solenberger | |
| 6,684,091 B2 | 1/2004 | Parker | |
| 6,731,963 B2 | 5/2004 | Finarov et al. | |
| 6,735,459 B2 | 5/2004 | Parker | |
| 6,745,061 B1 | 6/2004 | Hicks et al. | |
| 6,850,789 B2 | 2/2005 | Schweitzer, Jr. et al. | |
| 6,985,764 B2 | 1/2006 | Mason et al. | |
| 6,993,372 B2 * | 1/2006 | Fine et al. | 600/335 |
| 7,047,054 B2 | 5/2006 | Benni | |
| 7,127,278 B2 | 10/2006 | Melker et al. | |
| 7,132,641 B2 | 11/2006 | Schulz et al. | |
| 7,190,986 B1 | 3/2007 | Hannula et al. | |
| 7,245,953 B1 | 7/2007 | Parker | |
| 7,313,427 B2 | 12/2007 | Benni | |
| 7,340,287 B2 | 3/2008 | Mason et al. | |
| 7,412,272 B2 | 8/2008 | Medina | |
| 2002/0116797 A1 | 8/2002 | Modgil et al. | |
| 2003/0036690 A1 * | 2/2003 | Geddes et al. | 600/323 |
| 2005/0228248 A1 * | 10/2005 | Dietiker | 600/323 |
| 2005/0234317 A1 | 10/2005 | Kiani | |
| 2006/0106294 A1 | 5/2006 | Maser et al. | |
| 2006/0155198 A1 * | 7/2006 | Schmid | 600/500 |
| 2006/0200029 A1 | 9/2006 | Evans et al. | |
| 2007/0027376 A1 | 2/2007 | Todokoro et al. | |
| 2007/0078311 A1 | 4/2007 | Al-Ali et al. | |
| 2007/0197887 A1 | 8/2007 | Lunak et al. | |
| 2007/0219440 A1 | 9/2007 | Hannula et al. | |
| 2008/0009691 A1 | 1/2008 | Parker | |
| 2008/0033264 A1 | 2/2008 | Lonneker-Lammers et al. | |
| 2008/0262328 A1 | 10/2008 | Adams | |

FOREIGN PATENT DOCUMENTS

| | | |
|---|---|---|
| EP | 204459 | 12/1986 |
| EP | 430340 | 6/1991 |
| EP | 1491135 | 12/2004 |
| EP | 1807001 | 7/2007 |
| JP | 2004089546 | 3/2004 |
| JP | 2004159810 | 6/2004 |
| JP | 2004329607 | 11/2004 |
| JP | 2005110816 | 4/2005 |
| JP | 2005125106 | 5/2005 |
| JP | 2006158555 | 6/2006 |
| WO | 9740741 | 11/1997 |
| WO | 9947039 | 9/1999 |
| WO | 0059374 | 10/2000 |
| WO | 2006064399 | 6/2006 |
| WO | 2006079862 A2 | 8/2006 |

* cited by examiner

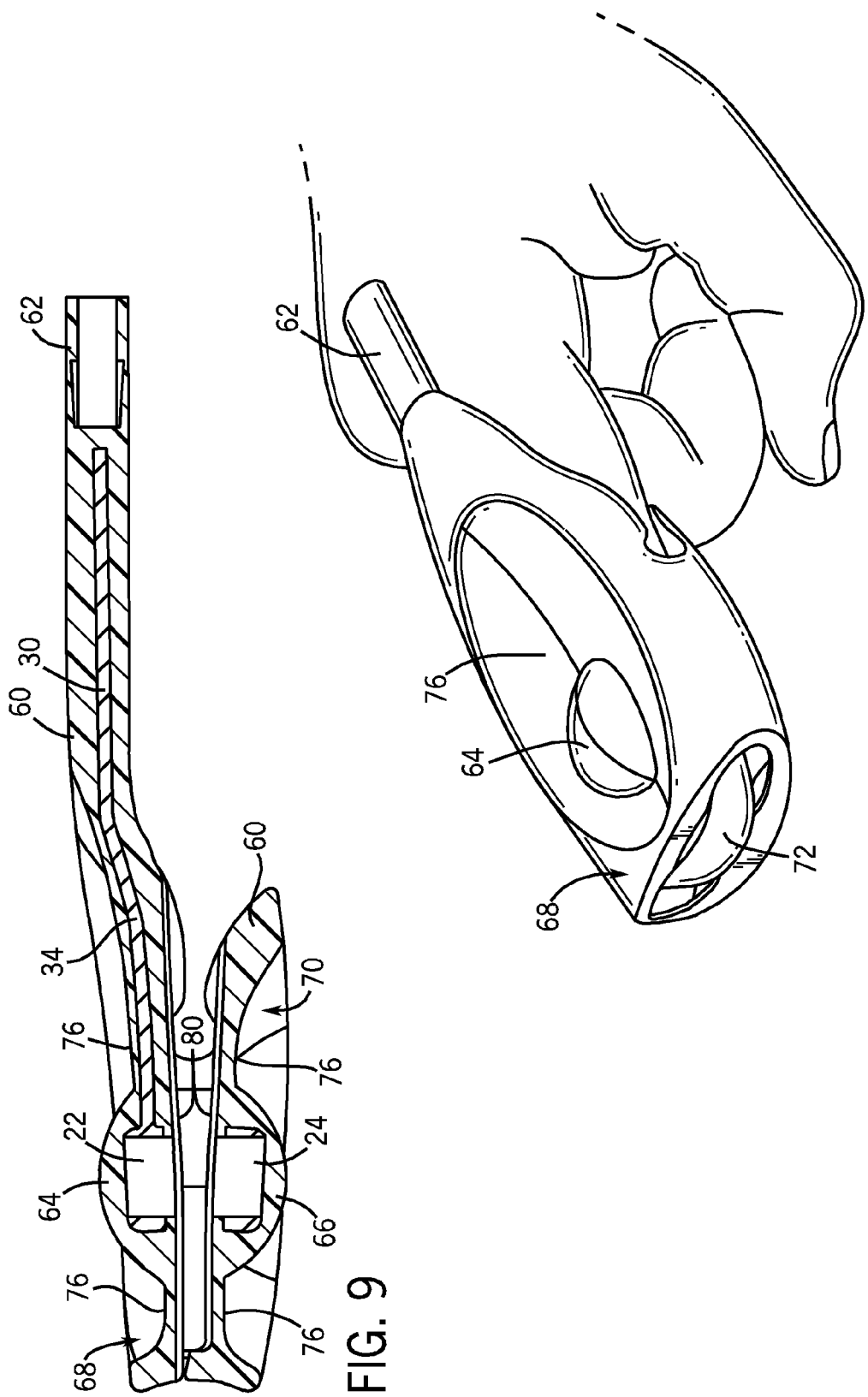

METHODS OF MANUFACTURING A COMPLIANT DIAPHRAGM MEDICAL SENSOR

CROSS-REFERENCE TO RELATED APPLICATION

This application is a divisional of U.S. application Ser. No. 12/491,061, filed on Jun. 24, 2009, which is a divisional of U.S. application Ser. No. 11/495,411, now U.S. Pat. No. 7,574,244, filed on Jul. 28, 2006, which is a continuation of U.S. application Ser. No. 11/199,345, now U.S. Pat. No. 7,657,294, filed Aug. 8, 2005, the disclosures of which are hereby incorporated by reference in their entirety for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, it may be desirable to employ, for cost and/or convenience, a pulse oximeter sensor that is reusable. Such reusable sensors, however, may be uncomfortable for the patient for various reasons. For example, the materials used in their construction may not be adequately compliant or supple or the structural features may include angles or edges.

Furthermore, the reusable sensor should fit snugly enough that incidental patient motion will not dislodge or move the sensor, yet not so tight that it may interfere with pulse oximetry measurements. Such a conforming fit may be difficult to achieve over a range of patient physiologies without adjustment or excessive attention on the part of medical personnel. In addition, lack of a tight or secure fit may allow light from the environment to reach the photodetecting elements of the sensor. Such environmental light is not related to a physiological characteristic of the patient and may, therefore, introduce error into the measurements derived using data obtained with the sensor.

Reusable pulse oximeter sensors are also used repeatedly and, typically, on more than one patient. Therefore, over the life of the sensor, detritus and other bio-debris (sloughed off skin cells, dried fluids, dirt, and so forth) may accumulate on the surface of the sensor or in crevices and cavities of the sensor, after repeated uses. As a result, it may be desirable to quickly and/or routinely clean the sensor in a thorough manner. However, in sensors having a multi-part construction, as is typical in reusable pulse oximeter sensors, it may be difficult to perform such a quick and/or routine cleaning. For example, such a thorough cleaning may require disassembly of the sensor and individual cleaning of the disassembled parts or may require careful cleaning using utensils capable of reaching into cavities or crevices of the sensor. Such cleaning is labor intensive and may be impractical in a typical hospital or clinic environment.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a sensor assembly that includes: a frame comprising a loop structure; an emitter and a detector disposed on opposing sides of the loop structure; and a coating provided over the frame, wherein the coating comprises at least one diaphragm structure disposed such that at least one of the emitter and the detector can move along an axis running between the emitter and the detector.

There is also provided a frame of a sensor that includes: a loop structure, wherein the loop structure is configured to provide support to an overlying coating when present such that one or more diaphragm structures are formed by the overlying coating.

There is also provided a method for manufacturing a frame of a sensor that includes: forming a frame comprising at least one loop structure, wherein the at least one loop structure is configured to provide support to an overlying coating when present such that one or more diaphragm structures are formed by the overlying coating.

BRIEF DESCRIPTION OF THE DRAWINGS

Advantages of the invention may become apparent upon reading the following detailed description and upon reference to the drawings in which:

FIG. 6 illustrates the overmolded patient sensor of FIGS. 4 and 5 in use on a patient's finger, in accordance with aspects of the present technique;

FIG. 9 illustrates a cross-section taken along section line 9-9 of the overmolded patient sensor depicted in FIG. 4.

DETAILED DESCRIPTION OF SPECIFIC EMBODIMENTS

Figure 1:
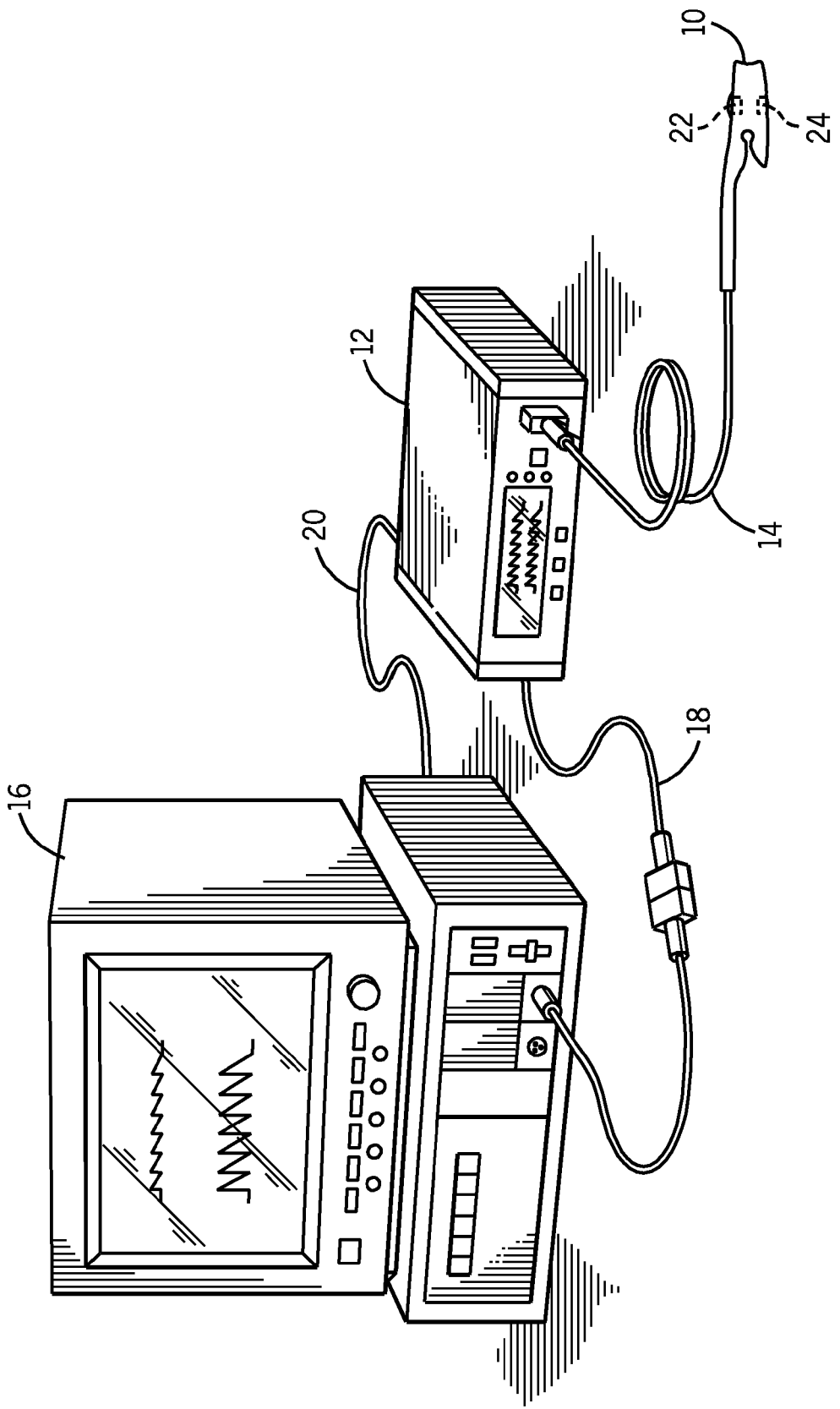
FIG. 1 illustrates a patient monitoring system coupled to a multi-parameter patient monitor and a sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a comfortable and conformable reusable patient sensor, such as for use in pulse oximetry or other applications utilizing spectrophotometry, that is easily cleaned and that is resistant to environmental light infiltration. In accordance with some aspects of the present technique, a reusable patient sensor is provided that is overmolded to provide patient comfort and a suitably conformable fit. The overmold material provides a seal against bodily fluids, as well as water or other cleaning fluids, that allows easy cleaning without disassembly or special tools. In accordance with some aspects of the present technique, the reusable patient sensor includes one or more diaphragm regions that provide expansion and conformability about the digit of a patient, thereby facilitating secure placement of the sensor on the patient.

Prior to discussing such exemplary sensors in detail, it should be appreciated that such sensors are typically designed for use with a patient monitoring system. For example, referring now to FIG. 1, a sensor 10 according to the present invention may be used in conjunction with a patient monitor 12. In the depicted embodiment, a cable 14 connects the sensor 10 to the patient monitor 12. As will be appreciated by those of ordinary skill in the art, the sensor 10 and/or the cable 14 may include or incorporate one or more integrated circuit devices or electrical devices, such as a memory, processor chip, or resistor that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors. In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12. As will be appreciated by those of ordinary skill in the art, the cable 14 (or corresponding wireless transmissions) are typically used to transmit control or timing signals from the monitor 12 to the sensor 10 and/or to transmit acquired data from the sensor 10 to the monitor 12. In some embodiments, however, the cable 14 may be an optical fiber that allows optical signals to be conducted between the monitor 12 and the sensor 10.

In one embodiment, the patient monitor 12 may be a suitable pulse oximeter, such as those available from Nellcor Puritan Bennett Inc. In other embodiments, the patient monitor 12 may be a monitor suitable for measuring tissue water fractions, or other body fluid related metrics, using spectrophotometric or other techniques. Furthermore, the monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 to provide additional functions, the patient monitor 12 may be coupled to a multi-parameter patient monitor 16 via a cable 18 connected to a sensor input port and/or via a cable 20 connected to a digital communication port.

The sensor 10, in the example depicted in FIG. 1, is overmolded to provide a unitary or enclosed assembly. The sensor 10, includes an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 that is responsible for transmitting electrical and/or optical signals to and from the emitter 22 and detector 24 of the sensor 10. The cable 14 may be permanently coupled to the sensor 10, or it may be removably coupled to the sensor 10—the latter alternative being more useful and cost efficient in situations where the sensor 10 is disposable.

The sensor 10 described above is generally configured for use as a "transmission type" sensor for use in spectrophotometric applications, though in some embodiments it may instead be configured for use as a "reflectance type sensor." Transmission type sensors include an emitter and detector that are typically placed on opposing sides of the sensor site. If the sensor site is a fingertip, for example, the sensor 10 is positioned over the patient's fingertip such that the emitter and detector lie on either side of the patient's nail bed. For example, the sensor 10 is positioned so that the emitter is located on the patient's fingernail and the detector is located opposite the emitter on the patient's finger pad. During operation, the emitter shines one or more wavelengths of light through the patient's fingertip, or other tissue, and the light received by the detector is processed to determine various physiological characteristics of the patient.

Reflectance type sensors generally operate under the same general principles as transmittance type sensors. However, reflectance type sensors include an emitter and detector that are typically placed on the same side of the sensor site. For example, a reflectance type sensor may be placed on a patient's fingertip such that the emitter and detector are positioned side-by-side. Reflectance type sensors detect light photons that are scattered back to the detector.

For pulse oximetry applications using either transmission or reflectance type sensors the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

Pulse oximetry and other spectrophotometric sensors, whether transmission-type or reflectance-type, are typically placed on a patient in a location conducive to measurement of the desired physiological parameters. For example, pulse oximetry sensors are typically placed on a patient in a location that is normally perfused with arterial blood to facilitate measurement of the desired blood characteristics, such as arterial oxygen saturation measurement ($SaO_2$). Common pulse oximetry sensor sites include a patient's fingertips, toes, forehead, or earlobes. Regardless of the placement of the sensor 10, the reliability of the pulse oximetry measurement is related to the accurate detection of transmitted light that has passed through the perfused tissue and has not been inappropriately supplemented by outside light sources or modulated by subdermal anatomic structures. Such inappropriate supplementation and/or modulation of the light transmitted by the sensor can cause variability in the resulting pulse oximetry measurements.

As noted above, the overmolded sensor 10 discussed herein may be configured for either transmission or reflectance type sensing. For simplicity, the exemplary embodiment of the sensor 10 described herein is adapted for use as a transmission-type sensor. As will be appreciated by those of ordinary skill in the art, however, such discussion is merely exemplary and is not intended to limit the scope of the present technique.

Figure 2:
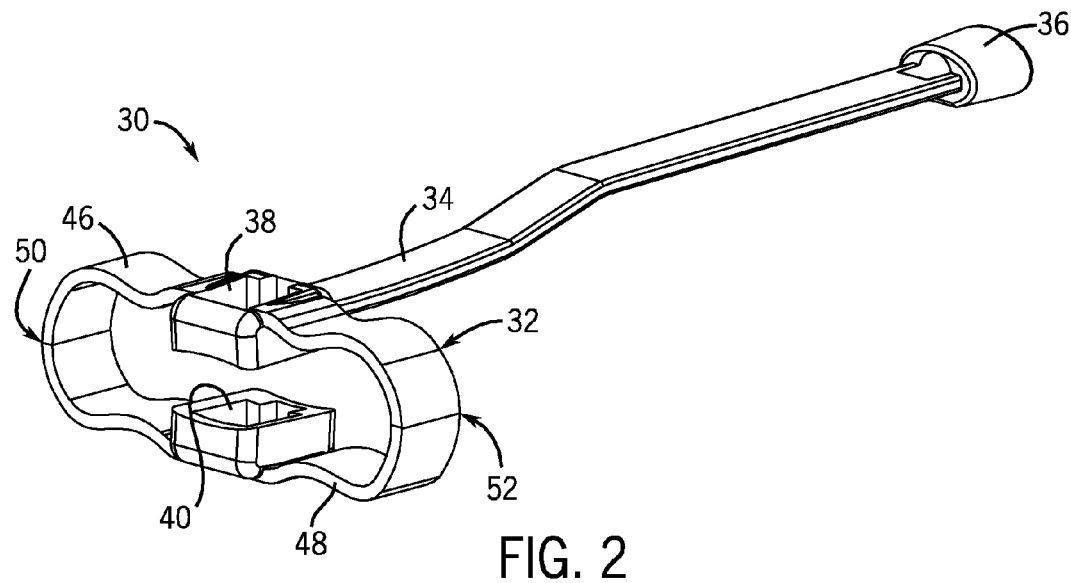
FIG. 2 illustrates a perspective view of an internal frame for use in a patient sensor, in accordance with aspects of the present technique.

Referring now to FIG. 2, an internal frame 30 for a sensor 10 is depicted. In the depicted example, the internal frame 30 is a skeletal frame for the sensor 10 in which one portion of the frame is formed as a loop 32. Such a skeletal frame may include different structures or regions that may or may not have similar rigidities. For example, the depicted skeletal frame includes the loop structure 32 and other structural supports 34 that define the general shape of the sensor 10 when coated, as discussed below with regard to FIGS. 3-9. In view of their structure providing function, the loop structure 32 and structural supports 34 may be constructed to be substantially rigid or semi-rigid. In addition, the loop structure 32 may act as a spring or biasing mechanism when coated, as discussed below, to bias the sensor 10 in the desired shape.

In addition, the skeletal frame may include a cable guide 36 through which a cable, such as an electrical or optical cable, may pass to connect to the electrical or optical conductors attached to the emitter 22 and/or detector 24 upon assembly. Likewise, a skeletal frame, such as the depicted internal frame 30, may include component housings, such as the emitter housing 38 and detector housing 40 which are attached to the remainder of the skeletal frame, such as via the loop structure 32. The loop structure 32 may be relatively flexible, allowing the emitter housing 38 and/or the detector housing 40 to move vertically (such as along an optical axis between the respective housings) relative to one another.

Figure 3:
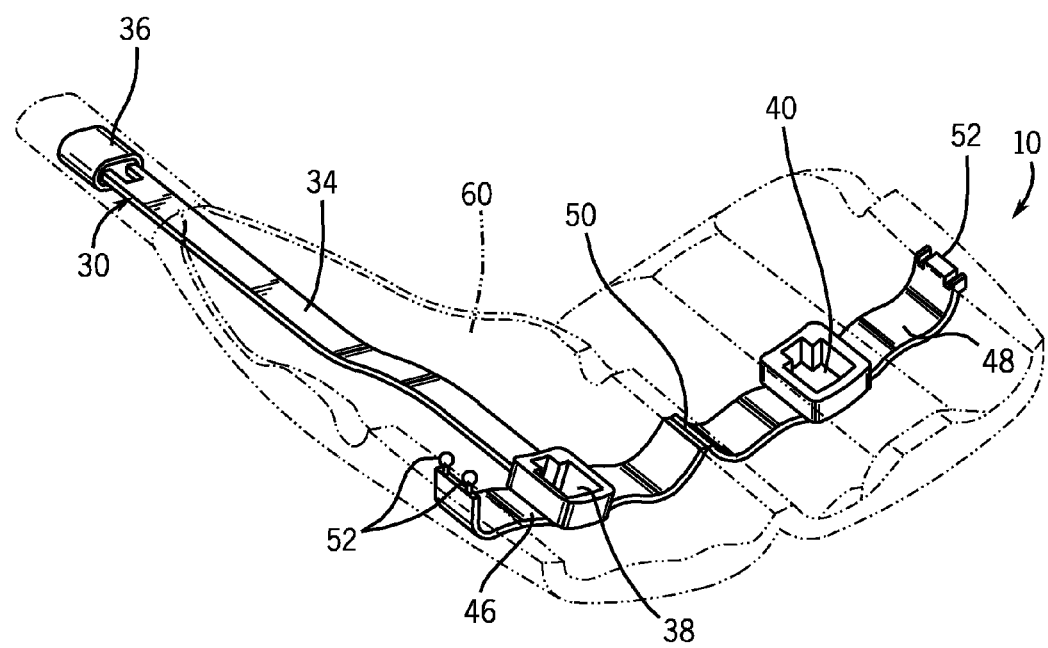
FIG. 3 illustrates a perspective view of the internal frame of FIG. 2 in an open configuration, in accordance with aspects of the present technique.

In embodiments where the internal frame 30 is skeletal, the various structural supports 34, housings 38 and 40, loop structure 32, and other structures may define various openings and spaces around and/or between the structures of the skeletal frame. In this manner, the skeletal frame provides structural support at specific locations for a coating or overmolding. However, in regions where structural support is not provided, flexibility and freedom of motion in an overlying coating or overmolding may be possible. For example, in one implementation, the emitter housing 38 and/or the detector housing 40 may be attached to the remainder of the skeletal frame by a flexible loop structure 32, as depicted in FIGS. 2 and 3. In such implementations, a coating 60 provided proximate to the emitter housing 38 and/or detector housing 40 may be sufficiently flexible (such as due to the elasticity and/or the thinness of the coating material in the open areas of the skeletal frame) such that the housings 38 and 40 may move independent of the remainder of the frame 30 along an optical axis between the housings 38 and 40.

In certain embodiments, the internal frame 30 is constructed, in whole or in part, from polymeric materials, such as thermoplastics, capable of providing a suitable rigidity or semi-rigidity for the different portions of the internal frame 30. Examples of such suitable materials include polypropylene, polyurethane, and nylon, though other polymeric materials may also be suitable. In other embodiments, the internal frame 30 is constructed, in whole or in part, from other suitably rigid or semi-rigid materials that provide the desired support and flexibility, such as stainless steel, aluminum, magnesium, graphite, fiberglass, or other metals, alloys, or compositions that are sufficiently ductile and/or strong. For example, metals, alloys, or compositions that are suitable for diecasting, sintering, lost wax casting, stamping and forming, and other metal or composition fabrication processes may be used to construct the internal frame 30.

In addition, the internal frame 30 may be constructed as an integral structure or as a composite structure. For example, in one embodiment, the internal frame 30 may be constructed as a single piece from a single material or from different materials. Alternatively, the internal frame 30 may be constructed or assembled from two or more parts that are separately formed. In such embodiments, the different parts may be formed from the same or different materials. For example, in implementations where different parts are formed from different materials, each part may be constructed from a material having suitable mechanical and/or chemical properties for that part. For example, the loop structure 32 may be formed to be more flexible than the structural support 34 of the frame 30. The different parts may then be joined or fitted together to form the internal frame 30.

In addition, the internal frame 30 may be molded, formed, or constructed in a different configuration than the final sensor configuration. For example, the internal frame 30 for use in the sensor 10 may be initially formed, from one or more pieces, in a generally open, or flat, configuration (as depicted in FIG. 3) compared to the relatively closed configuration of the internal frame 30 when folded to form the sensor 10 (as depicted in FIG. 2). In such embodiments, a top portion 46 and a bottom portion 48 of the internal frame 30 may be formed such that they are generally open or planar and are joined by a connective portion 50.

In such an implementation, the top portion 46, bottom portion 48, and connective portion 50 may be molded or formed as a single piece in an open configuration. In such an embodiment, the connective portion 50 may be broken or deformed to bring the top portion 46 and bottom portion 48 into a closed configuration, as depicted in FIG. 2. In this implementation, the top portion 46 and bottom portion 48 may be secured together, such as via a snap fitting process in which complementary connectors 52 (as depicted in FIG. 3) are snapped together to form a mechanical connection. Alternatively, the top portion 46 and bottom portion 48 may be secured together via other techniques suitable for attaching the respective portions of the internal frame 30, such as ultrasonic welding, or heat staking or by application of an adhesive or mechanical fastener.

Alternatively, the internal frame 30 may be formed as multiple parts that are joined together to form the internal frame 30. For example, the top portion 46 and the bottom portion 48 may be molded or formed separately and subsequently secured together to form the internal frame 30. The different parts of the internal frame 30 may be joined together using one or more of the techniques noted above, such as a snap fitting process, ultrasonic welding, or heat staking or by application of an adhesive or mechanical fastener. If the internal frame 30 is secured together in an open configuration, the connective portion 50 may be broken or deformed to bring the top portion 46 and bottom portion 48 into a closed configuration, as depicted in FIG. 2. Alternatively, the internal frame 30 may be constructed in a closed configuration from the separately molded or formed parts, such as the top portion 46 and bottom portion 48.

As noted above, in certain embodiments of the present technique, the frame 30 (such as a skeletal internal frame) is coated to form a unitary or integral sensor assembly as depicted in FIGS. 3-9. Such overmolded embodiments may result in a sensor assembly in which the internal frame 30 is completely or substantially coated. In embodiments in which the internal frame 30 is formed or molded as a relatively open or flat structure, the overmolding or coating process may be performed prior to or subsequent to bending the internal frame 30 into the closed configuration.

For example, the sensor 10 may be formed by an injection molding process. In one example of such a process the internal frame 30 may be positioned within a die or mold of the desired shape for the sensor 10. A molten or otherwise unset overmold material may then be injected into the die or mold. For example, in one implementation, a molten thermoplastic elastomer at between about 400° F. to about 450° F. is injected into the mold. The overmold material may then be set, such as by cooling for one or more minutes or by chemical treatment, to form the sensor body about the internal frame 30. In certain embodiments, other sensor components, such as the emitter 22 and/or detector 24, may be attached or inserted into their respective housings or positions on the overmolded sensor body.

Alternatively, the optical components (such as emitter 22 and detector 24) and/or conductive structures (such as wires or flex circuits) may be placed on the internal frame 30 prior to overmolding. The internal frame 30 and associated components may then be positioned within a die or mold and overmolded, as previously described. To protect the emitter 22, detector 24, and or other electrical components, conventional techniques for protecting such components from excessive temperatures may be employed. For example, the emitter 22 and/or the detector 24 may include an associated clear window, such as a plastic or crystal window, in contact with the mold to prevent coating from being applied over the window. In one embodiment, the material in contact with such windows may be composed of a material, such as beryllium copper, which prevents the heat of the injection molding process from being conveyed through the window to the optical components. For example, in one embodiment, a beryllium copper material initially at about 40° F. is contacted with the windows associated with the emitter 22 and/or detector 24 to prevent coating of the windows and heat transfer to the respective optical components. As will be appreciated by those of ordinary skill in the art, the injection molding process described herein is merely one technique by which the frame 30 may be coated to form a sensor body, with or without associated sensing components. Other techniques which may be employed include, but are not limited to, dipping the frame 30 into a molten or otherwise unset coating material to coat the frame 30 or spraying the frame 30 with a molten or otherwise unset coating material to coat the frame 30. In such implementations, the coating material may be subsequently set, such as by cooling or chemical means, to form the coating. Such alternative techniques, to the extent that they may involve high temperatures, may include thermally protecting whatever optical components are present, such as by using beryllium copper or other suitable materials to prevent heat transfer through the windows associated with the optical components, as discussed above.

Figure 4:
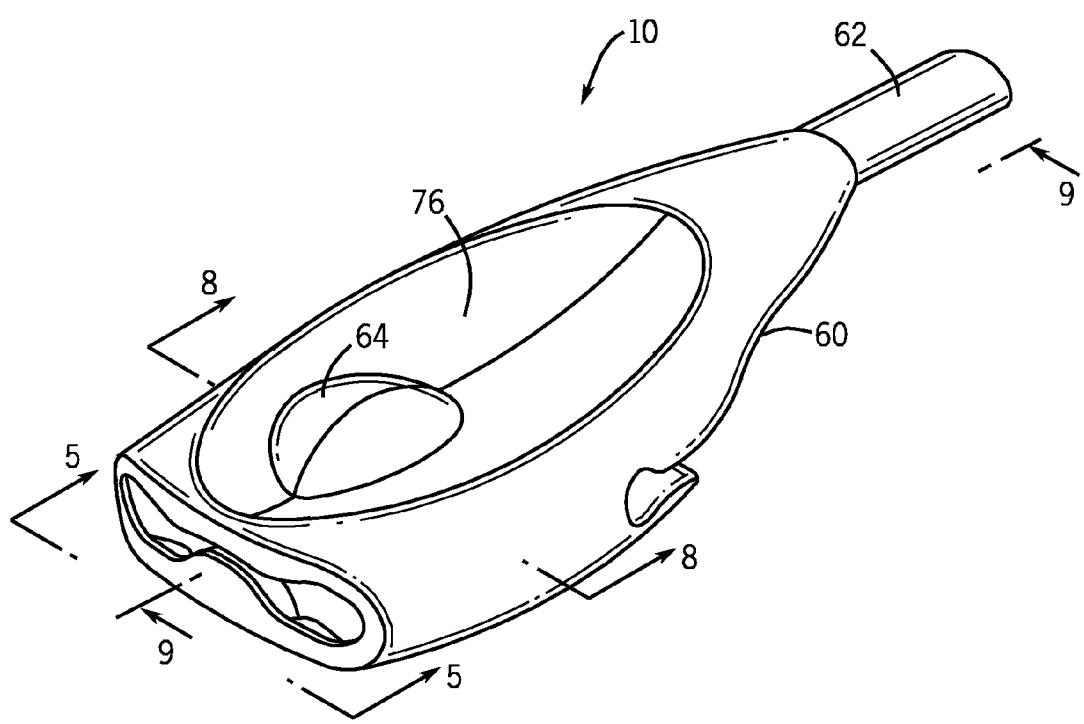
FIG. 4 illustrates a perspective view of an overmolded patient sensor, in accordance with aspects of the present technique.
Figure 5:
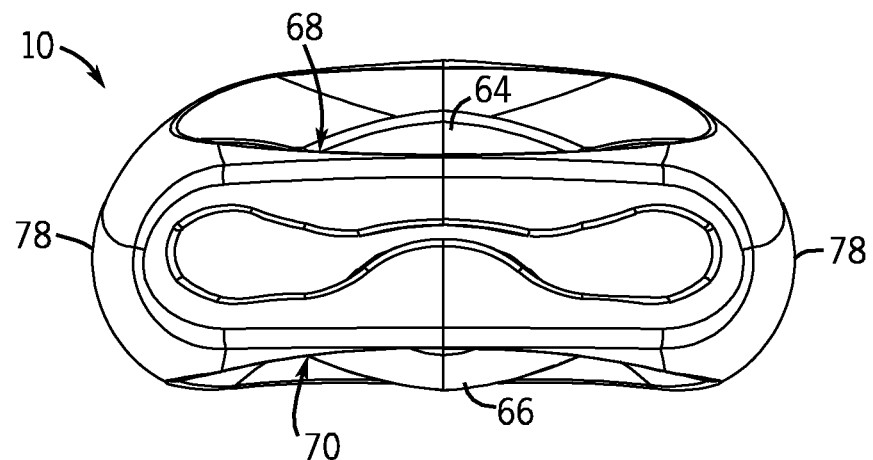
FIG. 5 illustrates a front view of the overmolded patient sensor of FIG. 4 taken along view line 5-5.
Figure 7:
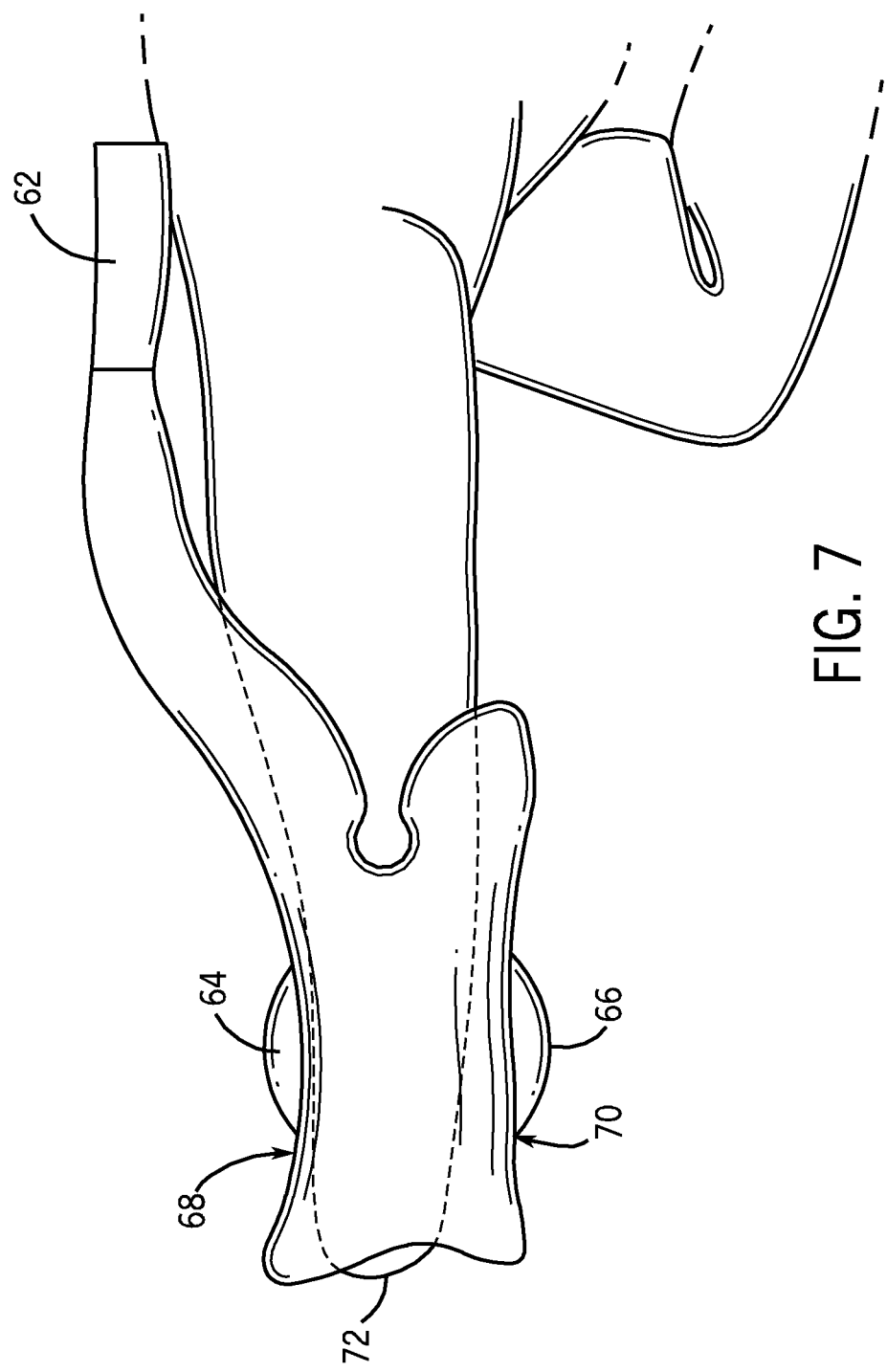
FIG. 7 illustrates a side view of the overmolded patient sensor of FIGS. 4 and 5 in use on a patient's finger, in accordance with aspects of the present technique.

By such techniques, the frame 30, as well as the optical components and associated circuitry where desired, may be encased in a coating material 60 to form an integral or unitary assembly with no exposed or external moving parts of the internal frame 30. For example, as depicted in FIGS. 4 and 5, the sensor 10 includes features of the underlying internal frame 30 that are now completely or partially overmolded, such as the overmolded external cable guide 62 and optical component housings, such as overmolded emitter housing 64 and detector housing 66. In addition, the overmolded sensor 10 includes an overmolded upper portion 68 and lower portion 70 that may be fitted about the finger 72 (as depicted in FIGS. 6 and 7) or to the toe or other appendage of the patient as appropriate.

In one implementation, the overmolding or coating 60 is a thermoplastic elastomer or other conformable coating or material. In such embodiments, the thermoplastic elastomer may include compositions such as thermoplastic polyolefins, thermoplastic vulcanizate alloys, thermoplastic polyurethane, silicone, and so forth. In one embodiment, the overmolding material is a thermoplastic elastomer having a durometer of about 15 to about 25 Shore. As will be appreciated by those of ordinary skill in the art, the overmolding composition may vary, depending on the varying degrees of flexibility, conformability, durability, wettability, or other physical and/or chemical traits that are desired. Furthermore, the coating material 60 may be selected based on the desired closing force imparted by the coating 60 to the upper portion 68 and lower portion 70 of the overmolded sensor body.

Furthermore, the coating material 60 may be selected based upon the desirability of a chemical bond between the internal frame 30 and the coating material 60. Such a chemical bond may be desirable for durability of the resulting overmolded sensor 10. For example, to prevent separation of the coating 60 from the internal frame 30, the material used to form the coating 60 may be selected such that the coating 60 bonds with some or all of the internal frame 30 during the overmolding process. In such embodiments, the coating 60 and the portions of the internal frame 30 to which the coating 60 is bonded are not separable, i.e., they form one continuous and generally inseparable structure.

Furthermore, in embodiments in which the coating 60 employed is liquid or fluid tight, such a sensor 10 may be easily maintained, cleaned, and/or disinfected by immersing the sensor into a disinfectant or cleaning solution or by rinsing the sensor 10 off, such as under running water. In particular, such an overmolded sensor assembly may be generally or substantially free of crevices, gaps, junctions or other surface irregularities typically associated with a multi-part construction which may normally allow the accumulation of biological detritus or residue. Such an absence of crevices and other irregularities may further facilitate the cleaning and care of the sensor 10.

Figure 8:
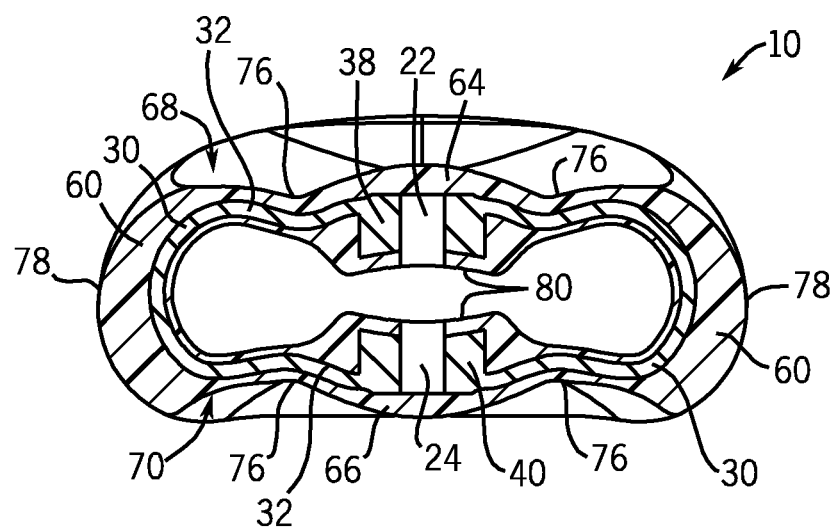
FIG. 8 illustrates a cross-section taken along section line 8-8 of the overmolded patient sensor depicted in FIG. 4.

Turning now to FIGS. 8 and 9, cross-sections of the coated sensor assembly 10 are depicted taken through transverse optical planes, represented by section lines 8 and 9 of FIG. 4 respectively. FIGS. 8 and 9 depict, among other aspects of the sensor 10, the overmolding material 60 as well as underlying portions of the internal frame 30, such as the emitter housing 38 and detector housing 40, along with the respective emitter 22, detector 24, and signal transmission structures (such as wiring or other structures for conducting electrical or optical signals). In the depicted embodiment, the emitter 22 and detector 24 are provided substantially flush with the patient facing surfaces of the sensor 10, as may be suitable for pulse oximetry applications. For other physiological monitoring applications, such as applications measuring tissue water fraction or other body fluid related metrics, other configurations may be desirable. For example, in such fluid measurement applications it may be desirable to provide one or both of the emitter 22 and detector 24 recessed relative to the patient facing surfaces of the sensor 10. Such modifications may be accomplished by proper configuration or design of a mold or die used in overmolding the internal frame 30 and/or by proper design of the emitter housing 38 or detector housing 40 of the internal frame 30.

In addition, as depicted in FIGS. 8 and 9, in certain embodiments portions of the coating material 60 may be flexible, such as thin or membranous regions of coating material 60 disposed about regions of the frame 30 and sensor 10 intended to flex. For example, in the depicted example, the overmolded detector housing 66 and emitter housing 64 are surrounded by comparatively thin and flexible dished regions that form diaphragm structures 76. In the depicted embodiment, opposing, co-axial diaphragm structures 76 are provided on both the top portion 68 and bottom portion 70 of the overmolded sensor 10. In addition, the diaphragm structures 76 may be symmetrical, such as round or elliptical structures. Such diaphragm structures 76 allow a greater range of digit sizes to be accommodated for a given retention or clamping force of the sensor 10. For example, the diaphragm structures 76 may allow the emitter 22 and/or detector 24, to flex or expand apart from one another along the optical axis in embodiments in which the respective housings 38 and 40 are flexibly attached to the remainder of the frame 30. In this manner, the sensor 10 may accommodate differently sized digits. For instance, for a relatively small digit, the diaphragm structures 76 may not be substantially deformed or vertically displaced, and therefore the emitter 22 and/or detector 24 are not substantially displaced either. For larger digits, however, the diaphragm structures 76 may be deformed or displaced to a greater extent to accommodate the digit, thereby displacing the emitter 22 and/or detector 24 as well. In addition, for medium to large digits, the diaphragm structures 76 may also increase retention of the sensor 10 on the digit by increasing the surface area to which the retaining force is applied.

Furthermore, as the diaphragm structures 76 deform, the force applied to the digit is spread out over a large area on the digit due to the deformation of the diaphragm structures 76. In this way, a lower pressure on digits of all sizes may be provided for a given vertical force. Therefore, a suitable conforming fit may be obtained in which the emitter 22 and detector 24 are maintained in contact with the digit without the application of concentrated and/or undesirable amounts of force, thereby improving blood flow through the digit.

In one embodiment, the loop structure 32 of the frame 30 and/or the coating material 60 bias the top portion 68 and a bottom portion 70 of the overmolded sensor 10 closed. An opposing force, however, may be applied to the lateral sides 78 of the overmolded sensor 10 to overcome the closing force and move the top portion 68 and bottom portion 70 apart. Alternately (or in addition), an opposing force may be applied to the inward facing surfaces 80 of the top portion 68 and bottom portion 70 to overcome the closing force and move the top portion 68 and bottom portion 70 apart. For example, in the depicted embodiment, the lateral sides 78 may be pinched or squeezed together to overcome the closing force provided by the frame 30 and the coating material 60 such that the top portion 68 and bottom portion 70 are separated. This process may be facilitated (or replaced) by the application of an opposing force to the inward facing surfaces 80 of the top portion 68 and bottom portion 70, such as by the insertion of a finger, to separate the top portion 68 and bottom portion 70. In this way, a patient sensor 10 incorporating the internal frame 30 may be opened for placement on a patient's finger, toe, or other appendage.

In the example depicted in FIGS. 8 and 9, the lateral sides 78 of the overmolding material facilitate the exclusion of environmental or ambient light from the interior of the sensor 10. In this manner, the lateral sides 78 help prevent or reduce the detection of light from the outside environment, which may be inappropriately detected by the sensor 10 as correlating to the $SaO_2$. Thus, a pulse oximetry sensor may detect differences in signal modulations unrelated to the underlying $SaO_2$ level. In turn, this may impact the detected red-to-infrared modulation ratio and, consequently, the measured blood oxygen saturation ($SpO_2$) value. The conformability of the fit of sensor 10 and the lateral sides 78, therefore, may help prevent or reduce such errors.

Though the preceding examples relate to embodiments having two opposing diaphragm structures 76 provided on opposing faces of the sensor 10, other embodiments are also presently contemplated. For example, in one alternative embodiment, a single diaphragm structure 76 is provided on either the top portion 68 or bottom portion 70, with the opposing portion being relatively rigid compared to the diaphragm containing portion. In such an embodiment, the diaphragm containing portion flexes in response to opposing lateral force, as discussed above, to provide a conforming and comfortable fit when applied to a patient.

While the exemplary medical sensors 10 discussed herein are some examples of overmolded or coated medical devices, other such devices are also contemplated and fall within the scope of the present disclosure. For example, other medical sensors and/or contacts applied externally to a patient may be advantageously applied using an overmolded sensor body as discussed herein. Examples of such sensors or contacts may include glucose monitors or other sensors or contacts that are generally held adjacent to the skin of a patient such that a conformable and comfortable fit is desired. Similarly, and as noted above, devices for measuring tissue water fraction or other body fluid related metrics may utilize a sensor as described herein. Likewise, other spectrophotometric applications where a probe is attached to a patient may utilize a sensor as described herein.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to retroflective and other sensor designs as well. Likewise, the present techniques are not limited to use on fingers and toes but may also be applied to placement on other body parts such as in embodiments configured for use on the ears or nose.

What is claimed is:

1. A method for manufacturing, comprising:
providing a frame comprising a loop structure and an emitter housing and a detector housing that protrude from an inner surface of the loop structure; and
forming a sensor body by applying a coating material over the frame, wherein the coating material covers at least one open area of the frame to provide at least one diaphragm structure, and wherein the sensor body is flexible such that the emitter housing and the detector housing are biased towards one another.

2. The method of claim 1, wherein providing the frame comprises performing at least one of a molding operation, a diecasting operation, a sintering operation, a casting operation, or a stamping operation.

3. The method of claim 1, wherein the frame is a unitary frame.

4. The method of claim 1, wherein frame comprises a plurality of pieces coupled to one another, and wherein each of the plurality of pieces comprise a thermoplastic material, a metal, a metallic alloy, or a composite material.

5. The method of claim 1, wherein the coating material covers two opposing open areas of the frame to provide two opposing diaphragm structures.

6. The method of claim 5, wherein the two opposing diaphragm structures correspond with the emitter housing and the detector housing, respectively.

7. The method of claim 1, wherein the loop structure is semi-rigid and the coating material is elastic such that the emitter housing and the detector housing are biased towards one another after applying the coating material.

8. The method of claim 1, wherein forming the sensor body comprises adhering the coating material to an outer surface of the frame.

9. The method of claim 1, wherein the at least one diaphragm structure is sufficiently elastic to enable the emitter housing and the detector housing move toward one another and away from one another without substantially moving a remainder of the frame.

10. The method of claim 1, comprising disposing an optical emitter in the emitter housing and an optical detector in the detector housing before applying the coating material over the frame.

11. The method of claim 10, wherein the optical emitter and the optical detector each comprise a clear plastic or crystal window that prevents the optical emitter and the optical detector from being covered by the coating material as the coating material is applied over the frame.

12. A method for manufacturing, comprising:
providing a frame comprising a loop structure and an emitter housing and a detector housing that protrude from an inner surface of the loop structure; and
forming a sensor body by applying a coating material over the frame, wherein the coating material covers at least one open area of the frame to provide at least one diaphragm structure, wherein the at least one diaphragm structure is sufficiently elastic to enable the emitter housing and the detector housing move toward one another and away from one another without substantially moving a remainder of the frame.

13. The method of claim 12, wherein the sensor body is flexible such that the emitter housing and the detector housing are biased towards one another.

14. The method of claim 12, comprising disposing an optical emitter in the emitter housing and an optical detector in the detector housing before applying the coating material over the frame.

15. The method of claim 14, wherein the optical emitter and the optical detector each comprise a clear plastic or crystal window that prevents the optical emitter and the optical detector from being covered by the coating material as the coating material is applied over the frame.

16. A method for manufacturing, comprising:
providing a frame comprising a loop structure and an emitter housing and a detector housing that protrude from an inner surface of the loop structure; and
disposing an optical emitter in the emitter housing and an optical detector in the detector housing and then forming a sensor body by applying a coating material over the frame, wherein the coating material covers at least one open area of the frame to provide at least one diaphragm structure.

17. The method of claim 16, wherein the optical emitter and the optical detector each comprise a clear plastic or crystal window that prevents the optical emitter and the optical detector from being covered by the coating material as the coating material is applied over the frame.

18. The method of claim 16, wherein the sensor body is flexible such that the emitter and the detector are biased towards one another.

19. The method of claim 16, wherein the at least one diaphragm structure is sufficiently elastic to enable the emitter housing and the detector housing move toward one another and away from one another without substantially moving a remainder of the frame.

20. The method of claim 16, wherein the loop structure is semi-rigid and the coating material is elastic such that the emitter and the detector are biased towards one another after applying the coating material.

* * * * *